(12) United States Patent
Patton

(10) Patent No.: US 7,524,300 B2
(45) Date of Patent: Apr. 28, 2009

(54) INFUSION DEVICE

(75) Inventor: Catherine C. Patton, Austin, TX (US)

(73) Assignee: Patton Medical Devices, LP, Austin, TX (US)

( * ) Notice: Subject to any disclaimer, the term of this patent is extended or adjusted under 35 U.S.C. 154(b) by 0 days.

(21) Appl. No.: 11/483,218

(22) Filed: Jul. 7, 2006

(65) Prior Publication Data

US 2006/0264818 A1 Nov. 23, 2006

Related U.S. Application Data

(62) Division of application No. 10/188,591, filed on Jul. 2, 2002, now Pat. No. 7,338,465.

(51) Int. Cl.
*A61M 31/00* (2006.01)

(52) U.S. Cl. .................... 604/93.01; 604/180

(58) Field of Classification Search ............ 604/93.01, 604/244, 246–247, 255, 288.01–288.04, 604/174–175, 180, 164.01, 167.01–167.04
See application file for complete search history.

(56) References Cited

U.S. PATENT DOCUMENTS

| 3,547,119 | A | 12/1970 | Hall et al. ............. 128/214.4 |
|---|---|---|---|
| 4,311,137 | A | 1/1982 | Gerard .................... 128/214.4 |
| 4,315,513 | A | 2/1982 | Nawash et al. ............ 128/348 |
| 4,525,164 | A | 6/1985 | Loeb et al. ................. 604/131 |
| 4,531,937 | A | 7/1985 | Yates ......................... 604/53 |
| 4,568,335 | A | 2/1986 | Updike et al. ............... 604/211 |
| 4,578,063 | A | 3/1986 | Inman et al. ............... 604/175 |
| 4,675,006 | A | 6/1987 | Hrushesky ................. 604/180 |
| 4,755,173 | A | 7/1988 | Konopka et al. ............ 604/167 |
| 4,772,261 | A | 9/1988 | Von Hoff et al. ............. 604/51 |
| 4,817,631 | A | 4/1989 | Schnepp-Pesch et al. ... 128/753 |
| 4,874,377 | A | 10/1989 | Newgard et al. ............ 604/167 |

(Continued)

FOREIGN PATENT DOCUMENTS

DE 19912459 A1 9/2000

(Continued)

OTHER PUBLICATIONS

"Insuflon" retrieved on Nov. 12, 2004 from http://www.poara.com/eng/insuflon/insuflon.htm.

(Continued)

*Primary Examiner*—Nicholas D Lucchesi
*Assistant Examiner*—Theodore J Stigell
(74) *Attorney, Agent, or Firm*—Fulbright & Jaworksi L.L.P.

(57) ABSTRACT

The disclosures made herein relate to an infusion device specifically adapted for syringe injections. In one embodiment of the disclosures made herein, an infusion device comprises a body including an accessible surface having a single inlet port therein, an engagement surface having a single outlet port therein, a medication delivery channel extending between the single inlet port and the single outlet port, and an identification feature on the accessible surface of the body adjacent to the single inlet port. The single inlet port of the medication delivery channel is tapered thereby forming a funnel-shaped entry into the medication delivery channel. A cannula is coupled to the body at the single outlet port and is adapted for receiving medication from the single outlet port and transmitting the medication therethrough.

18 Claims, 8 Drawing Sheets

U.S. PATENT DOCUMENTS

| | | | |
|---|---|---|---|
| 4,966,588 A | 10/1990 | Rayman et al. | 604/165.02 |
| 5,080,654 A | 1/1992 | Picha et al. | 604/167 |
| 5,092,849 A | 3/1992 | Sampson | 604/175 |
| 5,108,377 A | 4/1992 | Cone et al. | 604/175 |
| 5,122,114 A | 6/1992 | Miller et al. | 604/49 |
| 5,176,653 A | 1/1993 | Metals | 604/167.02 |
| 5,176,662 A | 1/1993 | Bartholomew et al. | 604/283 |
| 5,257,980 A | 11/1993 | Van Antwerp et al. | 604/506 |
| 5,306,243 A | 4/1994 | Bonaldo | 604/86 |
| 5,332,398 A | 7/1994 | Miller et al. | 604/175 |
| 5,342,316 A | 8/1994 | Wallace | 604/167 |
| 5,370,625 A | 12/1994 | Shickman | 604/174 |
| 5,409,466 A | 4/1995 | Watson et al. | 604/198 |
| 5,522,803 A | 6/1996 | Teissen-Simony | 604/177 |
| 5,545,143 A * | 8/1996 | Fischell | 604/180 |
| 5,545,152 A | 8/1996 | Funderburk et al. | 604/283 |
| 5,569,206 A | 10/1996 | Gorman et al. | 604/167.01 |
| 5,584,813 A | 12/1996 | Livingston et al. | 604/177 |
| 5,607,407 A | 3/1997 | Tolkoff et al. | 604/282 |
| 5,718,682 A | 2/1998 | Tucker | 604/93 |
| 5,797,879 A | 8/1998 | DeCampli | 604/93.01 |
| 5,848,989 A | 12/1998 | Villani | 604/288.02 |
| 5,851,197 A | 12/1998 | Marano et al. | 604/135 |
| 5,871,500 A | 2/1999 | Jepson et al. | 604/533 |
| 5,925,017 A | 7/1999 | Kriesel et al. | 604/132 |
| 5,951,521 A | 9/1999 | Mastrototaro et al. | 604/174 |
| 5,954,687 A * | 9/1999 | Baudino | 604/48 |
| 5,968,011 A * | 10/1999 | Larsen et al. | 604/288.02 |
| 5,980,506 A | 11/1999 | Mathiasen | 604/535 |
| 5,989,224 A | 11/1999 | Exline et al. | 604/167.02 |
| 6,017,328 A | 1/2000 | Fischell et al. | 604/180 |
| 6,056,718 A | 5/2000 | Funderburk et al. | 604/93.01 |
| 6,068,613 A | 5/2000 | Kriesel et al. | 604/132 |
| 6,074,371 A | 6/2000 | Fischell | 604/207 |
| 6,086,575 A | 7/2000 | Mejslov | 604/533 |
| 6,093,172 A | 7/2000 | Funderburk et al. | 604/135 |
| 6,110,154 A * | 8/2000 | Shimomura et al. | 604/256 |
| 6,123,690 A | 9/2000 | Mejslov | 604/283 |
| 6,176,235 B1 | 1/2001 | Benarrouch et al. | 128/200.24 |
| 6,254,586 B1 | 7/2001 | Mann et al. | 604/506 |
| 6,293,925 B1 | 9/2001 | Safabash et al. | 604/136 |
| 6,302,866 B1 | 10/2001 | Marggi | 604/174 |
| 6,355,021 B1 | 3/2002 | Nielsen et al. | 604/263 |
| 6,387,098 B1 | 5/2002 | Cole et al. | 606/62 |
| 6,413,244 B1 | 7/2002 | Bestetti et al. | 604/256 |
| 6,461,329 B1 | 10/2002 | Van Antwerp et al. | 604/111 |
| 6,488,663 B1 | 12/2002 | Steg | 604/164.08 |
| 6,520,938 B1 | 2/2003 | Funderburk et al. | 604/164.08 |
| 6,572,586 B1 * | 6/2003 | Wojcik | 604/165.01 |
| 6,579,267 B2 | 6/2003 | Lynch et al. | 604/174 |
| 6,629,949 B1 | 10/2003 | Douglas | 604/46 |
| 6,659,982 B2 | 12/2003 | Douglas et al. | 604/173 |
| 6,685,674 B2 | 2/2004 | Douglas et al. | 604/167.05 |
| 6,699,218 B2 | 3/2004 | Flaherty et al. | 604/131 |
| 6,736,797 B1 | 5/2004 | Larsen et al. | 604/167.05 |
| 6,749,587 B2 | 6/2004 | Flaherty | 604/151 |
| 6,749,589 B1 | 6/2004 | Douglas et al. | 604/165.01 |
| 6,805,693 B2 | 10/2004 | Gray et al. | 604/891.1 |
| 6,840,922 B2 | 1/2005 | Nielsen et al. | 604/263 |
| 6,960,192 B1 | 11/2005 | Flaherty et al. | 604/181 |
| 6,964,649 B2 | 11/2005 | Goll | 604/68 |
| 7,029,455 B2 | 4/2006 | Flaherty | 604/131 |
| 7,083,597 B2 | 8/2006 | Lynch et al. | 604/174 |
| 2001/0053887 A1 | 12/2001 | Douglas et al. | 604/152 |
| 2001/0053889 A1 | 12/2001 | Marggi et al. | 604/164.11 |
| 2001/0056064 A1 | 12/2001 | Aoki | 514/4 |
| 2002/0045867 A1 | 4/2002 | Nielsen et al. | 604/263 |
| 2002/0065484 A1 | 5/2002 | Douglas et al. | 604/93.01 |
| 2002/0072720 A1 | 6/2002 | Hague et al. | 604/264 |
| 2002/0072733 A1 | 6/2002 | Flaherty | 604/890.1 |
| 2002/0107476 A1 | 8/2002 | Mann et al. | 604/67 |
| 2002/0120231 A1 | 8/2002 | Douglas et al. | 604/82 |
| 2002/0123719 A1 | 9/2002 | Lavi et al. | 604/82 |
| 2002/0123740 A1 | 9/2002 | Flaherty et al. | 604/890.1 |
| 2002/0128600 A1 | 9/2002 | Nissels | 604/131 |
| 2002/0151855 A1 | 10/2002 | Douglas et al. | 604/218 |
| 2002/0161332 A1 | 10/2002 | Ramey | 604/164.07 |
| 2002/0173769 A1 | 11/2002 | Gray et al. | 604/506 |
| 2003/0023203 A1 | 1/2003 | Lavi et al. | 604/82 |
| 2003/0073952 A1 | 4/2003 | Flaherty et al. | 604/151 |
| 2003/0088238 A1 | 5/2003 | Poulsen et al. | 604/890.1 |
| 2003/0097092 A1 | 5/2003 | Flaherty | 604/67 |
| 2003/0100885 A1 | 5/2003 | Pettis et al. | 604/506 |
| 2003/0114751 A1 | 6/2003 | Pedain et al. | 600/431 |
| 2003/0199823 A1 | 10/2003 | Bobroff et al. | 604/136 |
| 2003/0212364 A1 | 11/2003 | Mann et al. | 604/131 |
| 2003/0213723 A1 | 11/2003 | Lombardi | 206/581 |
| 2003/0216686 A1 | 11/2003 | Lynch et al. | 604/93.01 |
| 2004/0015134 A1 | 1/2004 | Lavi et al. | 604/183 |
| 2004/0030285 A1 | 2/2004 | Lavi et al. | 604/82 |
| 2004/0073160 A1 | 4/2004 | Pinkerton | 604/28 |
| 2004/0143241 A1 | 7/2004 | Douglas et al. | 604/533 |
| 2004/0267238 A1 | 12/2004 | Haarala et al. | 604/502 |

FOREIGN PATENT DOCUMENTS

| | | |
|---|---|---|
| DE | 19912459 C2 | 2/2001 |
| EP | 1566193 | 8/2005 |
| FR | 2607012 | 5/1988 |
| JP | 59-118152 | 7/1984 |
| JP | 63-501405 | 2/1988 |
| JP | 03-126438 | 5/1991 |
| WO | WO 87/01041 | 2/1987 |
| WO | WO 88/03816 | 6/1988 |
| WO | WO 92/20400 | 11/1992 |

OTHER PUBLICATIONS

American Diabetes Association "Standards of medical care for patients with diabetes mellitus." *Diabetes Care*, 25:213-29, 2002.

Anderson DR, et al. "The use of an indwelling Teflon catheter for subcutaneous heparin administration during pregnancy. A randomized crossover study." *Arch. Intern. Med.*, 153:841-4, 1993.

FDA, Section 510(k) Notification for Viggio Insuflon, Aug. 24, 1998, Silver Spring, Maryland.

File History of U.S. Appl. No. 09/110,360, filed Jul. 6, 1998.

Hanas R, et al. "Side effects and indwelling times of subcutaneous catheters for insulin injections: a new device for injecting insulin with a minimum of pain in the treatment of insulin-dependent diabetes mellitus." *Diabetes Res. Clin. Pract.*, 10:73-83, 1990.

Hanas SR, et al. "Metabolic control is not altered when using indwelling catheters for insulin injections." *Diabetes Care*, 17:716-8, 1994.

Hanas SR, et al. "Unchanged insulin absorption after 4 days' use of subcutaneous indwelling catheters for insulin injections." *Diabetes Care*, 20:487-90, 1997.

Hanas, R. et al. "Experience of Pain from Insulin Injections Using Syringes Pens and Indwelling Catheters." Department of Pediatrics, Uddevalla Hospital, Uddevalla Sweden. Abstract. 1989.

Hanas, Ragnar et al. "X-ray appearance of the indwelling catheter when using insuflon for insulin injections." Department of Pediatrics Uddevalla Hospital, Uddevalla, Sweden. Abstracts of the 17th Annual Meeting of ISGD, Hormone Research 35:58, 1991.

Henry RR, et al. "Intensive conventional insulin therapy for type II diabetes. Metabolic effects during a 6-mo outpatient trial." *Diabetes Care*, 16:21-31, 1993.

Hunt LM, et al. "NIDDM patients' fears and hopes about insulin therapy. The basis of patient reluctance." *Diabetes Care*, 20:292-8, 1997.

Knip, Mikael et al. "No evidence of an accelerated absorption of exogenous insulin after using a subcutaneous catheter for 5 days in children with IDDM" *Diabetes Care*, June, 17:627, 1994.

Lamacraft G, et al. "Subcutaneous cannulae for morphine boluses in children: assessment of a technique," *J. Pain Symptom Manage.*, 13:43-9, 1997.

Liu D, et al. "Insulin absorption is faster when keeping the infusion site in use for three days during continuous subcutaneous insulin infusion." *Diabetes Res. Clin. Pract.*, 12:19-24, 1991.

Long AM, et al. "Indwelling cannula for insulin administration in diabetes mellitus." *Arch. Dis. Child*, 66:348-9, 1991.

McGrath PA, et al. "A new analogue scale for assessing children's pain: an initial validation study," *Pain*, Mar; 64:435-43, 1996.

Selam JL, et al. "Devices for insulin administration." *Diabetes Care*, 13:955-79, 1990.

Testa, Marcia A. et al. "Patient satisfaction with insulin therapy in type 2 diabetes: a randomized trial of injectable vs. inhaled insulin." *American Diabetes Association 62nd Annual Meeting and Scientific Sessions*, Jun. 14-18, 2002, San Francisco, CA, US.

Zambanini A, et al. "Injection related anxiety in insulin-treated diabetes." *Diabetes Res. Clin. Pract.*, 46:239-46, 1999.

Altman et al., "The Revised CONSORT Statement for Reporting Randomized Trials: Explanation and Elaboration," *Annals Internal Medicine*, 134:663-694, 2001.

Graham et al., "Control of Important Clinical Parameters for Patients with Type 2 Diabetes Mellitus," *Diabetes*, 51:A-274, 2002 (Abstract No. 1112-P).

Kaar et al., "Insulin Administration via a Subcutaneous Catheter: Effects on absorption," *Diabetes Care*, 16:1412-1413, 1993.

Su et al., "The Relationship between Regimen Burden and Psychological Well Being in Persons with Type 1 Diabetes: Inhaled vs Injectable Insulin," *American Diabetes Association 62nd Annual Meeting and Scientific Sessions*, San Francisco, CA, Jun. 14-18, 2002 (Abstract No. 1843-P, p. A448).

Taddio et al., "Use of lidocaine-priolcaine cream for vaccination pain in infants," *J. Pediatr.*, 124:643-648, 1994.

English Translation of Office Action issued in Japanese Application No. 2004-519654, mailed Apr. 28, 2008.

English Translation of Office Action issued in Japanese Application No. 2004-519654, mailed Nov. 25, 2008.

\* cited by examiner

INFUSION DEVICE

CROSS-REFERENCE TO RELATED APPLICATION

This is a divisional of application Ser. No. 10/188,591, filed Jul. 2, 2002 now U.S. Pat. No. 7,338,465, which is incorporated by reference without disclaimer.

FIELD OF THE DISCLOSURE

The disclosures herein relate generally to infusion devices and method, and more particularly to a subcutaneous infusion device specifically adapted for receiving therapeutic substances injected with a syringe.

BACKGROUND

Presently, the delivery options available to insulin dependent diabetics for insulin delivery include direct injections with a syringe, continuous-delivery with an insulin pump and injections with a jet-spray. Each one of these insulin delivery options has advantages, disadvantages and limitations with respect to factors such as convenience, cost, effort, safety, reliability and pain. Accordingly, selection of an acceptable delivery option by a diabetic will depend on the advantages of a selected insulin delivery option as well as the diabetic's ability and willingness to tolerate the limitations and disadvantages of the selected insulin delivery option.

One of the most reliable methods of insulin delivery that a diabetic can choose is direct injection with a syringe (i.e., an injection needle pierces the skin). Direct injection with a syringe offers precise measurement of insulin and the security of manual delivery. However, direct injection with a syringe sometimes necessitates multiple injections during the course of a day. For example, a Type-1 diabetic generally needs a dosage of insulin either immediately before or after a meal.

For many diabetics, their aversion to needles precludes them from ever being able to bring themselves to direct injection with a syringe. For other diabetics, multiple direct injections per day and bruises at the injection site become too much to tolerate. Regardless of the particular reason or reasons, there are a large number of diabetics who cannot bring themselves to inject their insulin directly with a needle or who lose their ability to tolerate direct injections with a syringe. These diabetics often under-medicate themselves, endangering their physical health and mental well being.

Many diabetics who choose not to subject themselves to multiple direct injections with a syringe, because they have a fear of needles and/or because they bruise easily, look to other options besides direct injections with a syringe. For those who simply have a fear of needles, but are able to tolerate the pain and bruises associated with injection needles, jet spray injection is an option. Jet spray injection delivers a fine stream of insulin through the skin under extreme high pressure. Although a needle is not used, jet spray injection exhibits a similar level of pain and bruising associated with its use as do direct injections with a syringe.

The insulin pump has become the most popular option for diabetics who cannot face multiple daily direct injections with a syringe. With the insulin pump, a diabetic receives a continuous dosage of insulin from a pump apparatus via an infusion device mounted on their body. Insulin is supplied (e.g., pumped) from the insulin pump through a tube to the infusion device. Infusion devices generally include a cannula mounting in a subcutaneous manner within the flesh of the diabetic. The infusion device includes a channel that transmits insulin from an inlet port to the cannula for being delivered to the subcutaneous tissue layer of the diabetic.

Mounting of the infusion device generally involves the use of an insertion needle. Most conventional infusion devices have an insertion needle that extends through a body of the device and through the cannula. During mounting of such a conventional infusion device, the insertion needle serves to pierce the skin and to support the cannula, as most cannulas are made from a soft and/or flexible material. Accordingly, the diabetic still must deal with a needle piecing their skin. However, because the infusion device may remain in place for an extended period of time (e.g., typically up to 3 days or more), the diabetic need only deal with one injection type needle over 3 or more days, rather than multiple times per day. This extended period of time between needle insertions is what makes the pump tolerable for many diabetics who have an aversion to being pierced with injection needles.

The advantages of the insulin pump do not come without a number of significant disadvantages. One disadvantage is that the precise measurement of insulin and the security of manual delivery associated with direct injections with a syringe are largely turned over to the insulin pump. Situations such as the pump malfunctioning, degradation of the insulin within the pump reservoir (e.g., due to heat), bubbles in the reservoir/supply tube of the pump (e.g., due to agitation) and inherent limitations of an electromechanical device often result in the pump delivering an incorrect dosage of insulin. As the pump is a continuous delivery device, the diabetic may not know that they are receiving an incorrect dosage of insulin until a lengthy period of time has passed, resulting in dangerous blood-sugar levels. Another disadvantage is that the insulin pump, which is about the size of a typical pager, must be worn essentially 24 hours per day. Finding an inconspicuous yet convenient place to wear the pump can be difficult. Still another disadvantage is the cost of the insulin pump—about $8000 for the pump, plus disposable supplies. Though insurance plans generally cover insulin pumps, the considerable price of the pump adversely affects insurance premiums. Furthermore, under certain insurance policies, the insured party may still have the responsibility of paying for at least a portion of the pump.

Therefore, a device and method for enabling a frequently administered medication to be injected with a syringe in a manner that overcomes limitations associated with conventional medication delivery devices and methods.

DETAILED DESCRIPTION OF THE FIGURES

Figure 1:
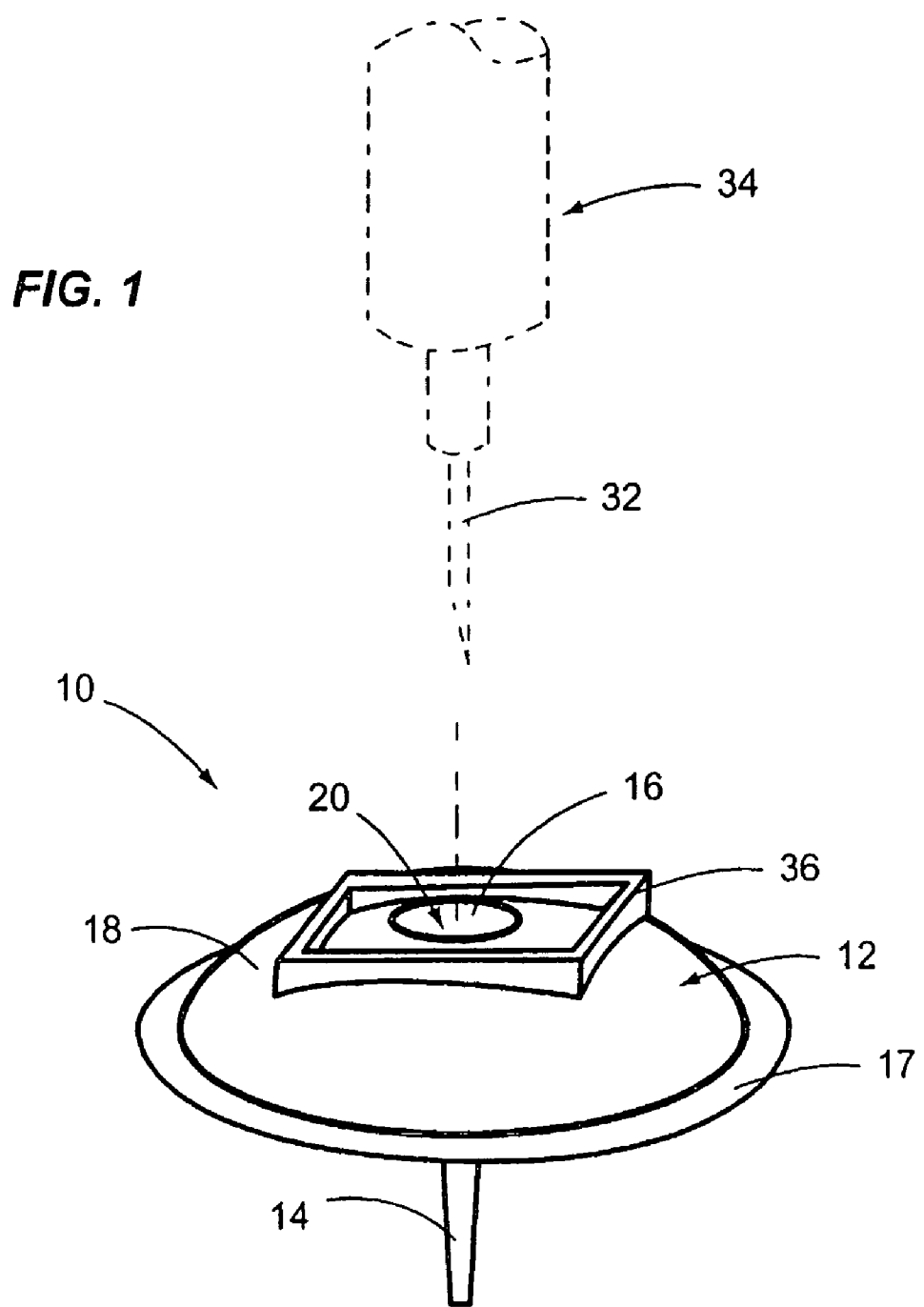
FIG. 1 is a perspective view depicting a single cannula infusion device in accordance with a first embodiment of the disclosures made herein.

The disclosures made herein relate to various aspects of an infusion device specifically adapted for receiving an injection from a syringe. As discussed in greater detail below, such an infusion device is beneficial to any patient (e.g., human patients or animal patients) that requires receiving medication via some type of direct injection on a daily basis. Insulin-dependent diabetics are an example of a patient that requires receiving medication via some type of trans-dermal medication delivery on a daily basis. In fact, a typical insulin-dependent diabetic require multiple trans-dermal injections of insulin daily.

An infusion device in accordance with embodiments of the disclosures made herein is mountable on a patient with the cannula extending into or through subcutaneous tissue of a patient. Once the infusion device is mounted on the patient, the patient may use a syringe and injection needle for receiving an injection of one or more medications via the infusion device. The patient is spared having their skin pierced by the injection needle. After an initial skin piercing by an insertion needle of the infusion device, all injections are facilitated via the injection needle being engaged with the infusion device rather than through the skin of the patient. The patient would only be subjected to piecing of the skin by a needle when replacing an existing mounted infusion device with a new infusion device. Depending on factors associated with the patient, the medication, the specific construction of the infusion device, it is contemplated herein that the infusion device would only need to be replaced every three days or more.

An infusion device in accordance with an embodiment of the disclosures made herein permits patients who might not otherwise choose direct injection with a syringe due to as their primary mode of medication delivery for any number of reasons (e.g., an aversion to needles, an intolerance to bruises at an injection site, etc) to now do so. Through the use of such an infusion device, a patient may enjoy the precise measurement of a medication and/or the security of manual delivery afforded by direct injection with a syringe. It should be noted that direct injection is one of the most reliable methods of self-delivery that a patient can choose. This reliability is due at least in part to this precise measurement of the medication and the security of manual delivery. In essence, a patient has direct control over when, where and how much medication they are receiving. Accordingly, infusion devices in accordance with embodiments of the disclosures made herein aid in enabling patients to properly medicate themselves, thus maintaining their health and mental well being.

Another advantage of an infusion device in accordance with an embodiment of the disclosures made herein is the ability to easily conceal the infusion device, without hindering access to it. The size and profile of the infusion device permits it to be worn inconspicuously under clothing at various portions of the patient's body. While not directly related to a patient's physiological health, being able to readily conceal the infusion device under nearly any garment goes a long way to enhancing the mental well-being of human patients.

Still another advantage of an infusion device in accordance with an embodiment of the disclosures made herein is its cost. Its cost is a fraction of other delivery devices intended to reduce anxiety and/or discomfort associated with direct injections with a syringe. Its relatively low cost will be of benefit to patients, doctors and insurance companies.

Figure 2:
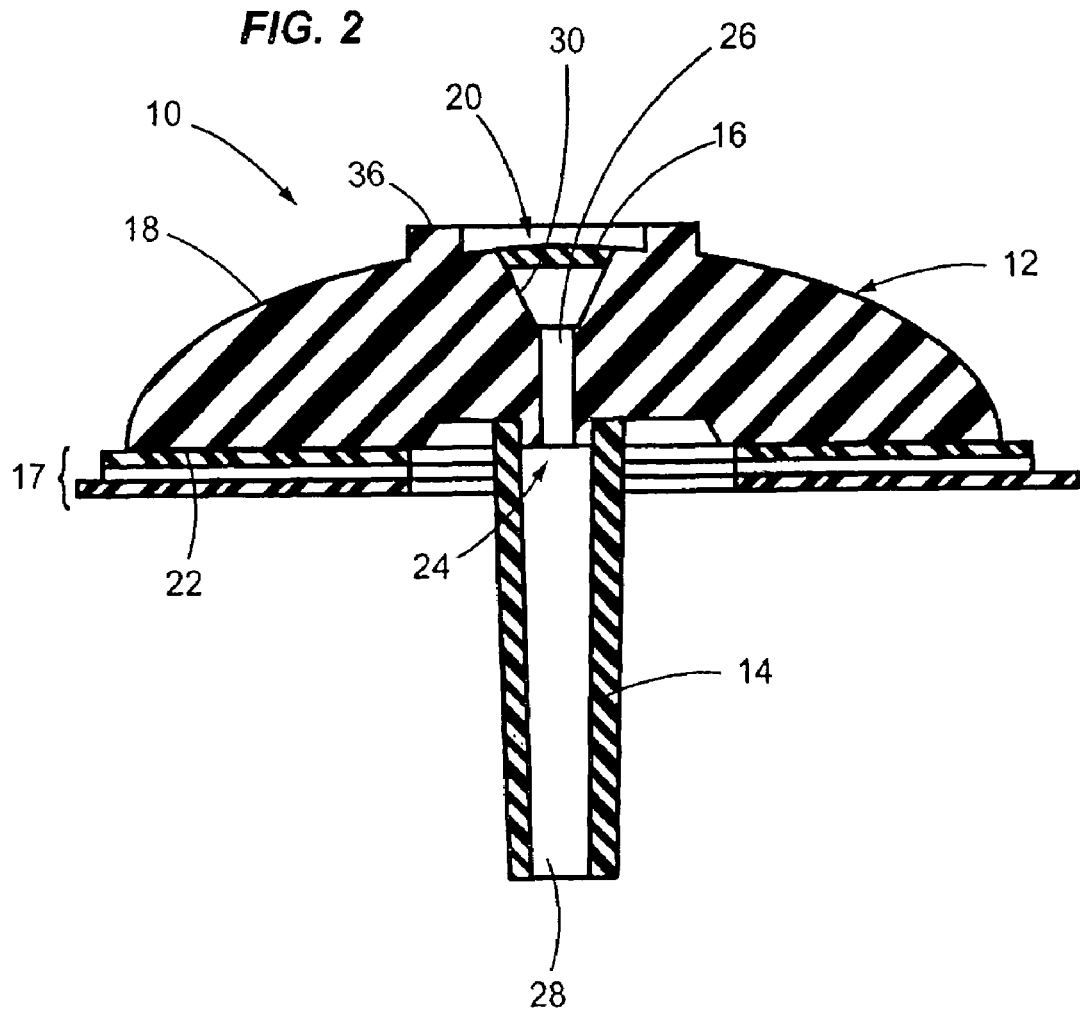
FIG. 2 is a cross-sectional view taken at the line 2-2 in FIG. 1.

Turning now to the drawing figures, FIGS. 1 and 2 depicts a infusion device 10 in accordance with a first embodiment of the disclosures made herein. The infusion device 10 includes a body 12, a cannula 14, a self-sealing member 16 and an adhesive laminate member 17. The body 12 includes an accessible surface 18 having a single inlet port 20 therein, an engagement surface 22 having a single outlet port 24 therein and a medication delivery channel 26 extending between the single inlet port 20 and the single outlet port 24. The infusion device 10 represents an embodiment of a single cannula infusion device in accordance with the disclosures made herein.

The cannula 14 is coupled to the body 12 at the single outlet port 24. The cannula 14 is adapted for receiving medication from the single outlet port 24 and transmitting the medication through a channel 28 of the cannula. The cannula 14 and the medication delivery channel 26 have an essentially straight, common longitudinal axis. The essentially straight, common longitudinal axis extends generally perpendicular to the engagement surface 22 of the body 12. Although the engagement surface 22 is depicted as being essentially planar, it is contemplated and disclosed herein that the engagement surface may have a profile other than essentially planar. Furthermore, it is contemplated herein that in other embodiments of infusion devices as disclosed herein, the medication delivery channel 26 and the associated cannula 14 do not have an essentially straight, common longitudinal axis.

The self-sealing member 16 is mounted at least partially within the medication delivery channel 26 with an exposed surface of the self-sealing member 16 being essentially contiguous with the accessible surface 18 of the body 12. The self-sealing member 16 forms a septum extending across the medication delivery channel 26. The septum limits contaminants entering the medication delivery channel 26 and limits the back-flow of medication from the medication delivery channel 26 through the single inlet port 20.

The adhesive laminate member 17 is mounted on the engagement surface 22 of the body 12. The adhesive laminate member 17 includes an adhesive layer disposed between a substrate layer and a release liner layer. The substrate layer provides structural integrity for the adhesive layer and is attached to the body 12. The release liner is removable from the adhesive layer for engaging the adhesive layer to be bonded to a skin surface of the patient during mounting of the infusion device 10, thereby securing the infusion device 10 to a patient's body. It is contemplated that the substrate layer may be omitted or integral with the body 12 in other embodiments (not shown) of the disclosures made herein.

The medication delivery channel 26 includes a tapered portion 30 adjacent to the accessible surface 18 of the body 12. The tapered portion 30 of the medication delivery channel 26 forms a funnel-shaped entry into the medication delivery channel 26. The tapered portion 30 is intended to aid a patient in engaging an injection needle 32 of a syringe 34 in a relatively quick and convenient manner by providing an insertion area for the needle 32 that is suitably larger than a cross sectional area of the injection needle 32.

The tapered portion 30 of the medication delivery channel 26 is tapered in a manner such that the single inlet port 20 has a minor diametrical dimension at least about two times greater than a minor diametrical dimension of the medication delivery channel 26. A nominal diametrical dimension of an essentially non-tapered portion of the medication delivery channel (e.g., adjacent to the single outlet port 24) is an example of the minor diametrical dimension of the medication delivery channel 26. Examples of port and channel cross-sectional profiles include round, rectangular, triangular, elliptical and other known profiles. In one embodiment of the single inlet port 20 and the medication delivery channel 26, the single inlet port 20 and the medication delivery channel 26 each have a substantially circular cross-sectional profile and the single inlet port 26 is essentially circular. In such an embodiment, the opening (i.e., a circular shaped opening) has a diameter at least about two times greater than a minor diameter of the medication delivery channel.

The body 12 further includes an identification feature 36 on the accessible surface 18 encompassing the single inlet port 20. The identification feature 36 is intended to aid in identifying the single inlet port 20. The identification feature 36 is raised with respect to the accessible surface 18 of the body 12.

It is contemplated herein that identification features in accordance with embodiments of the disclosures made herein may be at least partially raised with respect to an accessible surface of a respective body, may be at least partially recessed with respect to an accessible surface of a respective body or a combination of both raised and recessed with respect to an accessible surface of a respective body. It is also contemplated herein that identification features in accordance with embodiments of the disclosures made herein may be a different color than a respective body and/or self-sealing material. It is yet further contemplated herein that identification features in accordance with embodiments of the disclosures made herein may be any one of a plurality of shapes (e.g., round, rectangular, triangular, elliptical, etc.). It is still further contemplated herein that identification features in accordance with embodiments of the disclosures made herein may be a symbol (e.g., a Braille symbol) or a shape positioned adjacent to a respective inlet port, but not encompassing that port.

Figure 3:
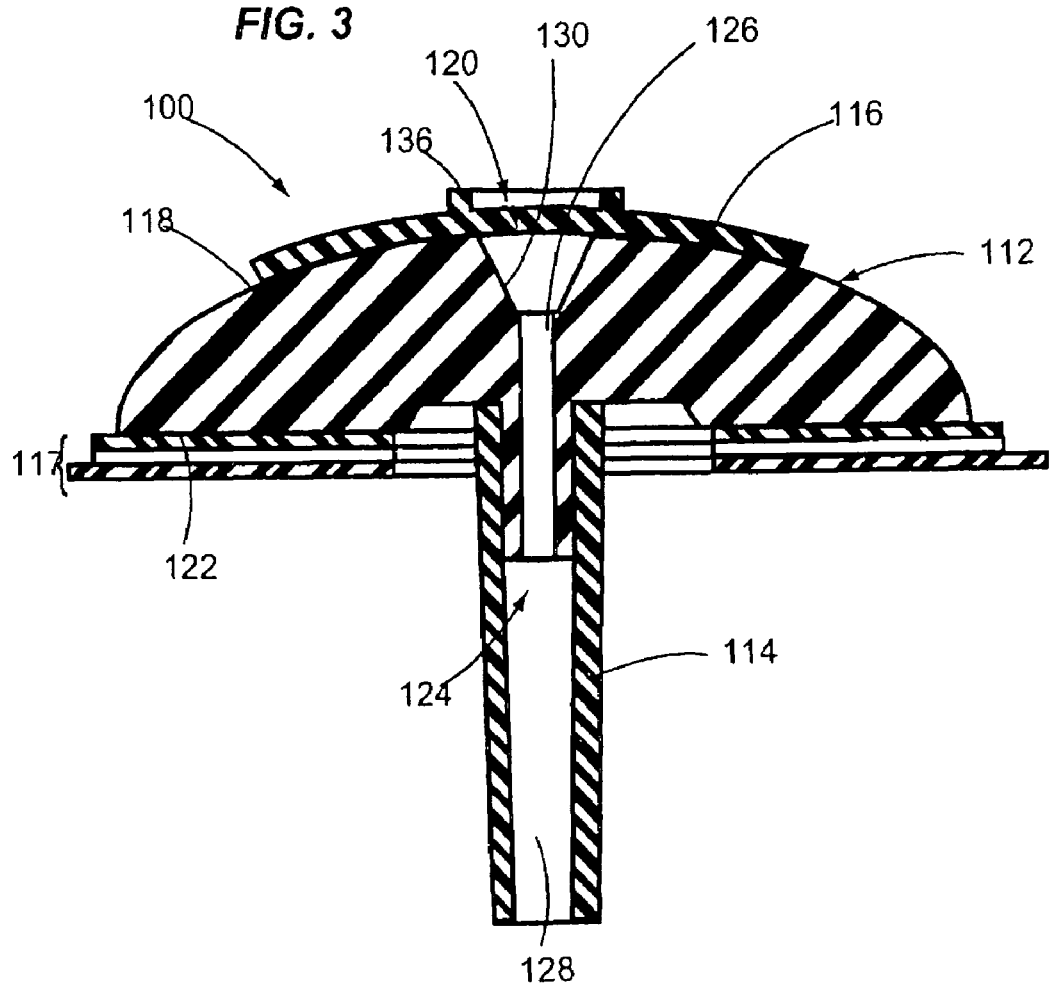
FIG. 3 is cross-sectional view depicting a single cannula infusion device in accordance with a second embodiment of the disclosures made herein, wherein the infusion device includes a self-sealing member mounted on an accessible surface a body of the infusion device and wherein the a single outlet port is offset from an engagement surface of the body.

FIG. 3 depicts an infusion device 100 in accordance with a second embodiment of the disclosures made herein. The infusion device 100 is similar in structure to the infusion device 10 depicted in FIGS. 1 and 2. Structural elements and features of the infusion device 100 and the infusion device 10 (depicted in FIGS. 1 and 2) are similarly denoted. For example, the body of the infusion device 100 is denoted as 112, whereas the body of the infusion device 10 is denoted as 12. Such similar elements and features are denoted for clarity in FIG. 3, but may not be discussed in specific detail in reference to FIG. 3.

The infusion device 100 includes a body 112, a self-sealing member 116 mounted on an accessible surface 118 of the body 112 and a single outlet port 124 that is offset from an engagement surface 122 of the body 112. The self-sealing member 116 forms a septum extending across the medication delivery channel 126. The septum limits contaminants entering the medication delivery channel 126 and limits the back-flow of medication from the medication delivery channel 126 through the single inlet port 120. Although the self-sealing member 116 is depicted as covering only a portion of the accessible surface 118 of the body 112, it is contemplated and disclosed herein that the self-sealing member 116 may cover essentially the entire accessible surface 118 of the body 112.

The self-sealing member 116 includes an integral identification feature 136. The identification feature 136 encompasses the single inlet port 120 of the medication delivery channel 126. The identification feature 136 is intended to aid in identifying the medication delivery channel 126. The identification feature 136 is raised with respect to an exposed surface of the self-sealing member 116. It is contemplated herein that identification features in accordance with embodiments of the disclosures made herein may be at least partially raised with respect to the exposed surface of a respective self-sealing member, may be at least partially recessed with respect to an exposed surface of a respective self-sealing member or a combination of both raised and recessed with respect to an exposed surface of a respective self-sealing member.

Figure 4:
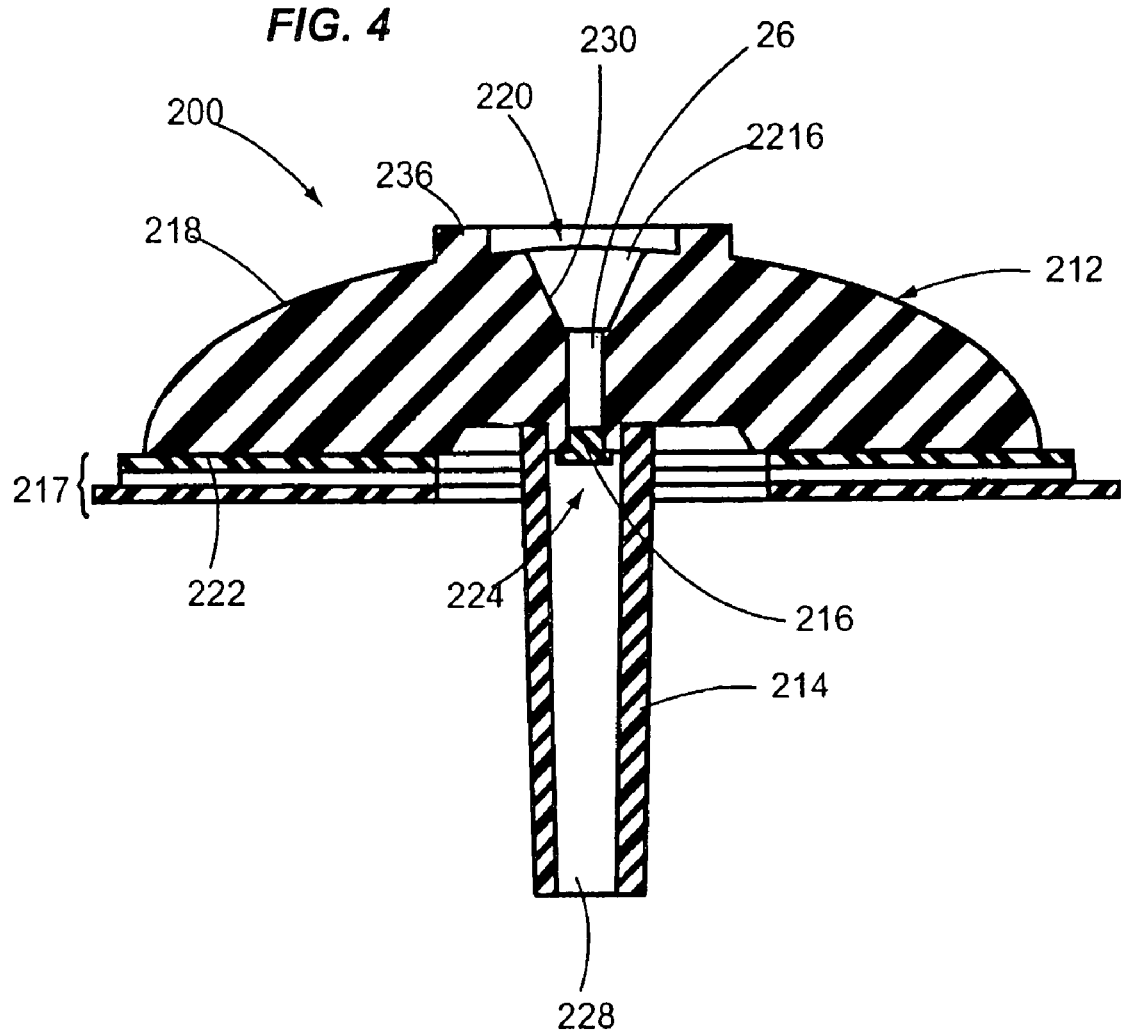
FIG. 4 is a cross-sectional view depicting a single cannula infusion device in accordance with a third embodiment of the disclosures made herein, wherein a self-sealing member is attached adjacent to an engagement surface of a body of the infusion device.

FIG. 4 depicts an infusion device 200 in accordance with a third embodiment of the disclosures made herein. The infusion device 200 is similar in structure to the infusion device 10 depicted in FIGS. 1 and 2. Structural elements and features of the infusion device 200 and the infusion device 10 (depicted in FIGS. 1 and 2) are similarly denoted. For example, the body of the infusion device 200 is denoted as 212, whereas the body of the infusion device 10 is denoted as 12. Such similar elements and features are denoted in FIG. 4, but may not be discussed in specific detail in reference to FIG. 4.

The infusion device 200 includes a body 212 and a self-sealing member 216. The self-sealing member 216 is mounted on the body 212 adjacent to an engagement surface 222 of the body 212 and at least partially within the medication delivery channel 226. The self-sealing member 216 forms a septum extending across the medication delivery channel 226 adjacent to a single outlet port 224 of the body 212. The septum limits contaminants entering the channel 228 of the cannula 214 and limits the back-flow of medication from the cannula through the single outlet port 224.

Figure 5:
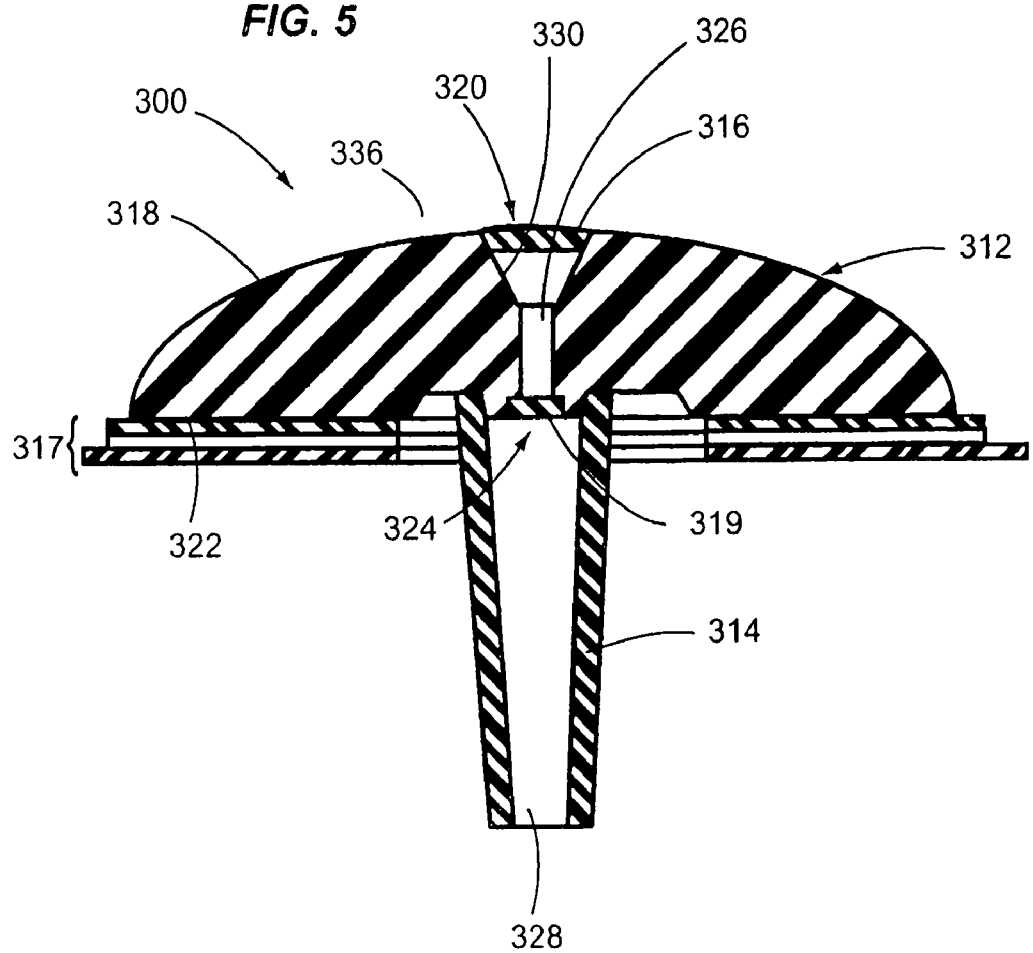
FIG. 5 is a cross-sectional view depicting a single cannula infusion device in accordance with a fourth embodiment of the disclosures made herein, wherein a first self-sealing member is attached adjacent to an accessible surface of a body of the infusion device and a second self-sealing member is attached adjacent to an engagement surface of the body of the infusion device.

FIG. 5 depicts an infusion device 300 in accordance with a fourth embodiment of the disclosures made herein. The infusion device 300 is similar in structure to the infusion device 10 depicted in FIGS. 1 and 2. Structural elements and features of the infusion device 300 and the infusion device 10 (depicted in FIGS. 1 and 2) are similarly denoted. For example, the body of the infusion device 300 is denoted as 312, whereas the body of the infusion device 10 is denoted as 12. Such similar elements and features are denoted in FIG. 5, but may not be discussed in specific detail in reference to FIG. 5.

The infusion device 300 includes a body 312, a first self-sealing member 316 mounted on the body 312 adjacent to an accessible surface 318 of the body 312 and a second self-sealing member 319 mounted on the body 312 adjacent to an engagement surface 322 of the body 312. The first self-sealing member 316 forms a septum extending across the medication delivery channel 326 adjacent to a single inlet port 320 of the body 312 (i.e., the first septum). The second self-sealing member 319 forms a septum extending across the medication delivery channel 326 adjacent to a single outlet port 324 of the body 312 (i.e., the second septum). The first septum limits contaminants entering the medication delivery channel 326 and limits the back-flow of medication from the medication delivery channel 326 through the single inlet port 320. The second septum limits the back-flow of medication from the medication delivery channel 326 through the single inlet port 320. An advantage of the second septum is that the volume of the medication delivery channel is taken out of the dosage amount (i.e., medication does not sit stagnant in the medication delivery channel) when the injection needle is properly inserted through both the first and the second septum prior to delivering the medication.

Figure 6:
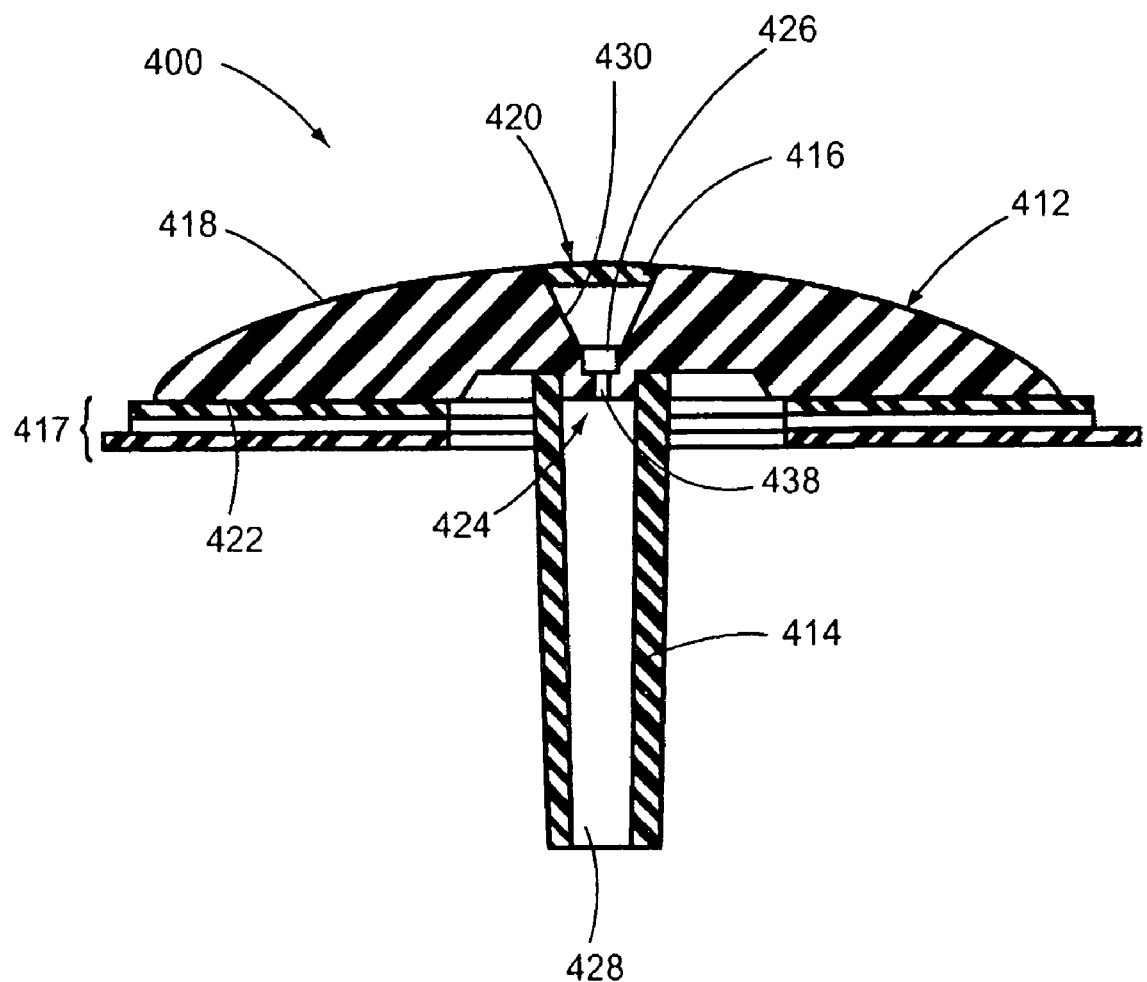
FIG. 6 is a cross-sectional view depicting a single cannula infusion device in accordance with a fifth embodiment of the disclosures made herein, wherein a needle stop is attached within a medication delivery channel of a body of the infusion device.

FIG. 6 depicts an infusion device 400 in accordance with a fifth embodiment of the disclosures made herein. The infusion device 400 is similar in structure to the infusion device 10 depicted in FIGS. 1 and 2. Structural elements and features of the infusion device 400 and the infusion device 10 (depicted in FIGS. 1 and 2) are similarly denoted. For example, the body of the infusion device 400 is denoted as 412, whereas the body of the infusion device 10 is denoted as 12. Such similar elements and features are denoted in FIG. 6, but may not be discussed in specific detail in reference to FIG. 6.

The infusion device 400 includes a body 412 having an accessible surface 418 with a single inlet port 420 therein, an engagement surface 422 having a single outlet port 424 therein and a medication delivery channel 426 extending between the single inlet port 420 and the single outlet port 424. A needle stop 438 is positioned adjacent to the single outlet port 424 of the medication delivery channel 426. The needle stop may be a discrete component attached to the body 412 or may be integrally formed with the body 412. The needle stop 438 limits the depth to which an injection needle can be inserted into the medication delivery channel 430.

One advantage of limiting the insertion depth of an insertion needle is that the needle is prevented from damaging (e.g., piercing) the cannula 414. Even when a needle that is too long relative to an intended use needle is used with the infusion device 400, the needle stop 438 precludes the needle from piercing through the cannula 414 or piercing into the patient's flesh adjacent to the cannula 414. Another advantage of limiting the insertion depth of an insertion needle is that the overall height of the body 412 can be reduced. Because the insertion depth of an injection needle is physically limited by the needle stop 438, the overall length of the medication delivery channel 426 (i.e., the distance between the single inlet port 420 and the single outlet port 424) no longer serves to limit over insertion of an injection needle. Accordingly, the overall height of the body 412 can be reduced with respect to a body without a needle stop, without concern for over insertion of an injection needle.

Figure 7:
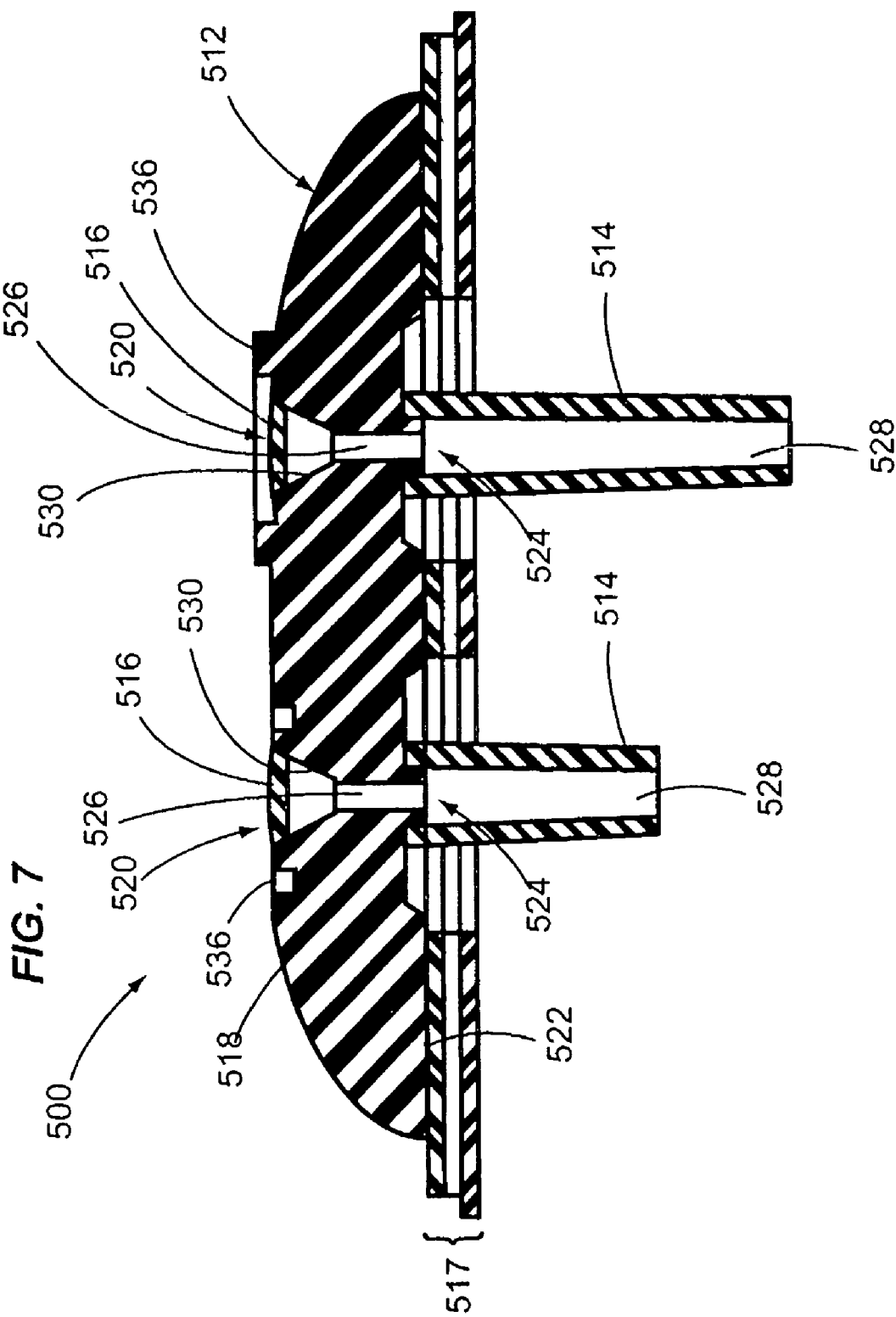
FIG. 7 is a cross-sectional view depicting a multi-cannula infusion device in accordance with a sixth embodiment of the disclosures made herein, wherein a plurality of self-sealing members are mounted adjacent to respective medication delivery channels and wherein a first cannula is a different length than a second cannula.

FIG. 7 depicts an infusion device 500 in accordance with a sixth embodiment of the disclosures made herein. The infusion device 500 includes a body 512, a plurality of cannulas 514, a plurality of self-sealing members 516 and an adhesive laminate member 517. The body 512 includes an accessible surface 518 having a plurality of single inlet ports 520 therein, an engagement surface 522 having a plurality of single outlet ports 524 therein and a discrete medication delivery channel 526 extending between a respective one of the single inlet ports 520 and a respective one of the single outlet ports 524. Each discrete medication channel 526 is associated with only one of the single inlet ports 520 and only one of the single outlet ports 524.

Each discrete medication delivery channel 526 is spaced apart from an adjacent discrete medication delivery channel 526 by a prescribed distance. Factors such as the type(s) of medication and the frequency of injections delivered via the infusion device 500 influence the prescribed distance. The term discrete in reference to medication delivery channel refers to each medication delivery channel being separate from each other medication delivery channel. The infusion device 500 represents an embodiment of a multi-cannula infusion device in accordance with the disclosures made herein.

Each one of the cannulas 514 is coupled to the body 512 at a respective one of the single outlet ports 524. Each one of the cannulas 514 is adapted for receiving medication from the respective one of the single outlet ports for transmitting the medication through a channel 528 of the corresponding one of the cannulas 514. A first one of the cannulas 514 is a different length than a second one of the cannulas. It is contemplated that in other embodiments of multi-cannula infusion devices in accordance with the disclosures made herein, all of the cannulas are essentially the same length.

Each medication delivery channel 526 and the associated one of said cannulas 514 have a common, essentially straight longitudinal axis. The common, essentially straight longitudinal axis extends generally perpendicular to the engagement surface 522 of the body 512. Although the engagement surface 522 is depicted as being essentially planar, it is contemplated and disclosed herein that the engagement surface 522 may have a profile other than essentially planar. Furthermore, it is contemplated herein that in other embodiments of an infusion device (not shown), each medication delivery channel and the associated one of the cannulas 514 do not have an essentially straight longitudinal axis.

Each one of the self-sealing members 516 is mounted within a respective medication delivery channel 526 with an exposed surface of each one of the self-sealing members 516 being essentially contiguous with the accessible surface 518 of the body 512. Each one of the self-sealing members 516 forms a septum extending across the respective medication delivery channel 526. Each septum limits contaminants entering the medication delivery channel 526 and limits the backflow of medication from the medication delivery channel 526 through the respective one of the single inlet ports 20.

The adhesive laminate member 517 is mounted on the engagement surface 522 of the body 512. The adhesive laminate member 517 includes an adhesive layer disposed between a substrate layer and a release liner layer. The substrate layer provides structural integrity for the adhesive layer and is attached to the body 512. The release liner is removable from the adhesive layer for engaging the adhesive layer to be bonded to a skin surface of the patient during mounting of the infusion device 500, thereby securing the infusion device 500 to a patient's body.

Each medication delivery channel 526 includes a tapered portion 530 adjacent to the accessible surface 518 of the body 512. The tapered portion 530 of each medication delivery channel 526 forms a funnel-shaped entry into the respective medication delivery channel 526. The tapered portion 530 of each medication delivery channel 526 is intended to aid a patient in engaging an injection needle of a syringe in a relatively quick and convenient manner by providing an insertion area for the needle that is suitably larger than a cross sectional area of the injection needle.

The tapered portion 530 of each medication delivery channel 526 is tapered in a manner such that the respective one of the single inlet ports 520 has a minor diametrical dimension at least about two times greater than a minor diametrical dimension of the same medication delivery channel 526. A nominal diametrical dimension of an essentially non-tapered portion of the medication delivery channel (e.g., adjacent to the single outlet port 524) is an example of the minor diametrical dimension of the medication delivery channel 526. Examples of port and channel cross-sectional profiles include round, rectangular, triangular, elliptical and other known profiles. In one embodiment of the single inlet ports 520 and each medication delivery channel 526, each one of the single inlet ports 520 and each medication delivery channel 526 have a substantially circular cross-sectional profile and the single inlet port 526 is essentially circular. In such an embodiment, the opening (i.e. a circular shaped opening) has a diameter at least about two times greater than a minor diameter of the medication delivery channel.

The body 512 further includes a plurality of identification features 536 on the accessible surface 518. Each one of the identification features 536 encompasses a respective one of the single inlet ports 520. Each one of the identification features 536 is intended to aid in identifying the respective one of the single inlet ports 530. A first one of the identification features 536 is raised with respect to the accessible surface 518 of the body 512 and a second one of the identification features 536 is recessed with respect to the accessible surface 518 of the body 512.

It is contemplated herein that identification features in accordance with embodiments of the disclosures made herein may be at least partially raised with respect to an accessible surface of a respective body, may be at least partially recessed with respect to an accessible surface of a respective body or a combination of both raised and recessed with respect to an accessible surface of a respective body. It is also contemplated herein that identification features in accordance with embodiments of the disclosures made herein may be a different color than a respective body and/or self-sealing material. It is yet further contemplated herein that identification features in accordance with embodiments of the disclosures made herein may be any one of a plurality of shapes (e.g., round, rectangular, triangular, elliptical, etc.).

Figure 8:
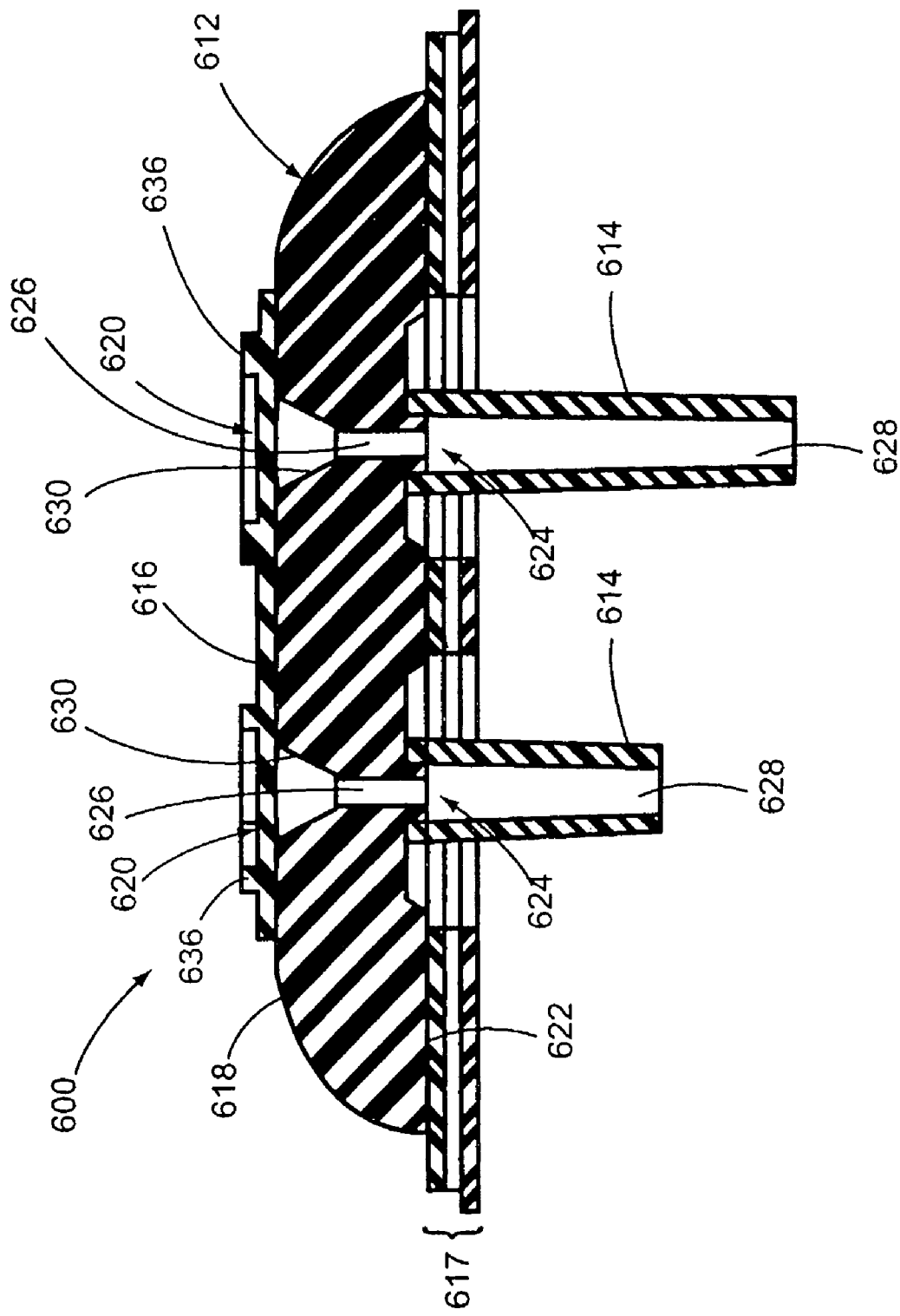
FIG. 8 is a cross-sectional view depicting a multi-cannula infusion device in accordance with a seventh embodiment of the disclosures made herein, wherein a single self-sealing member is attached to an accessible surface of a body of the infusion device thereby forming a septum for each one of a plurality of medication delivery channels.

FIG. 8 depicts an infusion device 600 in accordance with a seventh embodiment of the disclosures made herein. The infusion device 600 is similar in structure to the infusion device 500 depicted in FIG. 7. The infusion device 500 depicted in FIG. 7 and the infusion device 600 depicted in FIG. 8 are both multi-cannula infusion devices. Structural elements and features of the infusion device 600 and the infusion device 10 (depicted in FIGS. 1 and 2) are similarly denoted. For example, the body of the infusion device 600 is denoted as 612, whereas the body of the infusion device 500 is denoted as 512. Such similar elements and features are denoted in FIG. 8, but may not be discussed in specific detail in reference to FIG. 8.

The infusion device 600 includes a body 612 and a self-sealing member 616 mounted on an accessible surface 618 of the body 612. The body includes a plurality of inlet ports 620, a plurality of outlet ports 624 and a plurality of discrete medication delivery channels 626. Each one of the discrete medication delivery channels is connected between a respective one of the inlet ports 620 and a respective one of the outlet ports 624. The self-sealing member 616 forms a septum extending across a plurality of the medication delivery channels 626. Although the self-sealing member 616 is depicted as covering only a portion of the accessible surface 618 of the body 612, it is contemplated and disclosed herein that the self-sealing member 616 may cover essentially the entire accessible surface 618 of the body 612. The self-sealing member 616 includes a plurality of integral identification features 636. One or both of the identification features 636 encompasses a respective one of the inlet ports 620. The identification feature 636 toward the left side of FIG. 8 is depicted as being a polygon.

It is contemplated herein that structural elements and features discussed herein in reference to single cannula infusion devices of FIGS. 1 through 6, but not specifically discussed in reference to multi-cannula infusion devices, may be applied to multi-cannula infusion devices in accordance with embodiments of the disclosures made herein. For example, a needle stop may be applied to a multi-cannula infusion device in accordance with an embodiment of the disclosures made herein. Similarly, a septum may be provides at each outlet port.

It is also contemplated herein that a first structural element or features discussed herein in reference to a particular embodiment of a single cannula infusion device may be implemented in combination with a second structural element or feature discussed herein in reference to another particular embodiment of a single cannula infusion device, even though such combination is not specifically shown. One example would include implementing a needle stop in combination with a self-sealing member that is mounted on the accessible surface of a body. Another example would include implementing a self-sealing member mounted on the accessible surface of a body in combination with a self-sealing member that is mounted adjacent to an engagement surface of the body.

Infusion devices in accordance with embodiments of the disclosures made herein are capable of being fabricated using known techniques for forming elements of such infusion devices and for assembling such elements. Injection molding, extrusion, thermal forming and the like are examples of known techniques for forming such elements. Heat staking, ultrasonic welding, laser welding, solvent bonding and the like are examples of known techniques for assembling such components.

Infusion devices in accordance with embodiments of the disclosures made herein are capable of being fabricated from commercially available materials. Various polymers approved for use in medication applications by the United States Food and Drug Administration (U.S.F.D.A) are examples of commercially available material from which elements of infusion devices may be made. For example, a material approved by the U.S.F.D.A. for use in invasive medical application is an example of a material from which cannula may be made. Materials approved by the U.S.F.D.A. for being exposed to therapeutic substances, but not approved for use in invasive applications, are examples of materials from which the body and septum may be made. In cases where the body and/or a septum of the infusion device are subjected to invasive conditions, a material approved by the U.S.F.D.A. for use in invasive medical application is appropriate.

It will be appreciated that infusion devices in accordance with embodiments of the disclosures made herein provide a reliable, safe, easy, fast, convenient and painless approach to delivering medications such as insulin. Overall training and equipment costs are greatly reduced through the use of such infusion devices. Additionally, such infusion devices provide great psychological benefits for patients, resulting from eliminating discomfort and mental distress often associated with direct injections with a syringe. Generally speaking, such infusion devices will contribute to enhancing the overall quality of life of many patients that require daily injections of medication.

Single cannula and multi-cannula infusion devices in accordance with embodiments of the disclosures made herein are subcutaneous infusion sites capable of being self-mounted by a patient. In one embodiment of mounting such a single cannula or multi-cannula infusion device, an insertion device capable of inserting the cannula into the subcutaneous tissue of the patient under a force applied by a spring, by air or the like may be used. Various embodiments of insertion devices are known. It will be appreciated by a person of ordinary skill in the art that such known insertion devices may require certain modification for use with infusion devices in accordance with embodiments of the disclosures made herein.

Single cannula and multi-cannula infusion devices in accordance with embodiments of the disclosures made herein are intended to be worn and are capable of being worn for multiple days. Such infusion devices permit daily direct injections with a syringe into the subcutaneous tissue of the patient, thereby precluding daily pain and discomfort associated with injection needles. In this manner, the benefits of delivering a medication with a direct injection are provided, but without the drawbacks (e.g., multiple daily piercing of the skin). With an infusion device in accordance to an embodiment of the disclosures made herein, the skin need only be pierced about every three days or more for facilitating the associated direct inject.

A single cannula infusion device in accordance with an embodiment of the disclosures made herein is particularly well-suited for enabling a patient to receive a single type of medication (e.g., insulin). However, if the patient is required to inject multiple types of medication that are not compatible with each other (e.g., a bolus-type insulin and a Basal-type insulin), it is contemplated and disclosed herein that the patient may use sterile saline solution to flush the single cannula infusion device between injections of different medications.

Multi-cannula infusion devices represent another option for facilitating the delivery of multiple medications. A first medication can be delivered via a first cannula and a second medication can be delivered via a second cannula. Similarly, by distributing a plurality of injections of a particular medication between a plurality of single cannula infusion devices, the length of time that each of the plurality of single cannula infusion devices may be worn is extended.

It is also contemplated that a multi-cannula infusion device in accordance with an embodiment of the disclosures made herein or a plurality of single cannula devices may be used for extending the length of time that the infusion device may be worn. Tissue damage associated with pressure of delivering a medication and with the concentration of the medication are limiting factors in how long an infusion device may be worn and/or used. Accordingly, by distributing a plurality of injections of a particular medication between a plurality of cannulas, the length of time that the infusion device may be worn is extended.

An embodiment of a method for distributing a plurality of medication injections using a multi-cannula infusion device as disclosed herein includes mounting a multi-cannuia infusion device on a patient. An embodiment of mounting the multi-cannula infusion device includes inserting each one of the cannulas into subcutaneous tissue of the patient until an engagement surface of a body of the infusion device engages a skin surface of the patient. The multi-cannula infusion device includes a plurality of insertion needles for facilitating its mounting. Each one of the insertion needles extends through a channel of a respective one of the cannulas for retaining the respective one of the cannulas in a generally straight orientation during insertion.

After mounting the multi-cannula infusion device on the patient and removing the plurality of insertion needles, a first portion of a plurality of medication injections are administered to the patient via a first medication delivery channel of the multi-cannula infusion device and a second portion of the plurality of medication injections to the patient via a second medication delivery channel of the multi-cannula infusion device. A length of the first one of the cannulas is greater than a length of the second one of the cannulas, thereby enabling the first portion of the plurality of medication injections to be delivered at a first distance below a skin surface of the patient and enabling the second portion of the plurality of medication injections to be delivered at a second distance below the skin surface of the patient.

An embodiment of a method for distributing a plurality of medication injections using a plurality of single cannula infusion devices as disclosed herein includes mounting a plurality of single cannula infusion devices on a patient. An embodiment of mounting each one of the single cannula infusion devices includes inserting the cannula of each one of the single cannula infusion devices into subcutaneous tissue of the patient until an engagement surface of a body of each single cannula infusion device engages a skin surface of the patient. Each one of the single cannula infusion device includes an insertion needles for facilitating its mounting. Each one of the insertion needles extends through a channel of a respective one of the cannulas for retaining the respective one of the cannulas in a generally straight orientation during insertion.

In one embodiment of mounting the plurality of infusion devices, a first one of the infusion devices is mounted at a first location on the patient and a second one of the infusion devices is mounted at a second location on the patient. A first physiological portion of the patient such as a first leg is an example of the first location. A second physiological portion of the patient such as a left hip is an example of the second location.

After mounting the plurality of single cannula infusion devices on the patient and removing the insertion needles from each of the infusion devices, a first portion of a plurality of medication injections are administered to the patient via a first cannula of the multi-cannula infusion device and a second portion of the plurality of medication injections to the patient via a second cannula of the multi-cannula infusion device. A length of the cannula of the first infusion device is greater than a length of the cannula of the second infusion device, thereby enabling the first portion of the plurality of medication injections to be delivered at a first distance below a skin surface of the patient and enabling the second portion of the plurality of medication injections to be delivered at a second distance below the skin surface of the patient.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. To avoid unnecessary detail, the description omits certain information known to those skilled in the art. For example, certain dimensions of elements of an infusion device, certain orientations of elements, specific selection of materials for various elements and the like may be implemented based on an engineering preference and/or a specific application requirement. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. An infusion device comprising:
a body having a body passageway, a top, and a bottom surface, the body having an outermost perimeter;
an adhesive layer attached to the bottom surface;
a cannula coupled to the body and having a portion extending from the body and being positioned such that any portion of the cannula that is above a patient's skin when the infusion device is used is positioned within the outermost perimeter, the cannula also having a cannula passageway defined at least in part by a cannula passageway wall that has a greatest cannula passageway wall width, an upper cannula passageway wall portion that will not be in direct contact with medication delivered through the infusion device and into a living being when the infusion device is used, and a lower cannula passageway wall portion that will be in direct contact with medication delivered through the infusion device and into a living being when the infusion device is used;

a self-sealing septum that is separate from but coupled to the body, the septum having a septum bottom surface that includes a septum bottom surface portion that is exposed to open space that is (a) upstream of and in fluid communication with the lower cannula passageway wall portion and (b) within the body passageway, the septum also having a septum top surface that includes a septum top surface portion accessible to an injection needle, the septum top surface portion being defined by a septum top surface portion perimeter having a greatest width that is greater than the greatest cannula passageway wall width of the cannula; and an inner surface that directly borders open space within the body passageway that is downstream of the septum and upstream of the lower cannula passageway wall portion, the inner surface having an inwardly-tapered portion.

2. The infusion device of claim 1, in which at least a portion of the septum is bounded by a portion of the body.

3. The infusion device of claim 2, in which the septum includes an outer wall extending from the septum bottom surface, the outer wall including an inwardly-tapered portion.

4. The infusion device of claim 3, in which the infusion device includes (a) a first distance between the septum top surface and the top of the body and (b) a second distance between the septum bottom surface and the bottom surface of the body, and the second distance is greater than the first distance.

5. The infusion device of claim 2, in which the infusion device includes (a) a first distance between the septum top surface and the top of the body and (b) a second distance between the septum bottom surface and the bottom surface of the body, and the second distance is greater than the first distance.

6. The infusion device of claim 1, in which the septum includes an outer wall extending from the septum bottom surface, the outer wall including an inwardly-tapered portion.

7. The infusion device of claim 6, in which the infusion device includes (a) a first distance between the septum top surface and the top of the body and (b) a second distance between the septum bottom surface and the bottom surface of the body, and the second distance is greater than the first distance.

8. The infusion device of claim 1, in which the infusion device includes (a) a first distance between the septum top surface and the top of the body and (b) a second distance between the septum bottom surface and the bottom surface of the body, and the second distance is greater than the first distance.

9. The infusion device of claim 1, in which the adhesive layer is attached to the bottom surface through a substrate layer.

10. The infusion device of claim 9, further comprising a release liner attached to the adhesive layer.

11. An infusion device comprising:
a body having a body passageway, a top, and an adhesive bottom surface, the body having an outermost perimeter;
a cannula coupled to the body and having a portion extending from the body and being positioned such that any portion of the cannula that is above a patient's skin when the infusion device is used is positioned within the outermost perimeter, the cannula also having a cannula passageway defined at least in part by a cannula passageway wall that has a greatest cannula passageway wall width, an upper cannula passageway wall portion that will not be in direct contact with medication delivered through the infusion device and into a living being when the infusion device is used, and a lower cannula passageway wall portion that will be in direct contact with medication delivered through the infusion device and into a living being when the infusion device is used;

a self-sealing septum that is separate from but coupled to the body, the septum having a septum bottom surface that includes a septum bottom surface portion that is exposed to open space that is (a) upstream of and in fluid communication with the lower cannula passageway wall portion and (b) within the body passageway, the septum also having a septum top surface that includes a septum top surface portion accessible to an injection needle, the septum top surface portion being defined by a septum top surface portion perimeter having a greatest width that is greater than the greatest cannula passageway wall width of the cannula; and an inner surface that directly borders open space within the body passageway that is downstream of the septum and upstream of the lower cannula passageway wall portion, the inner surface having an inwardly-tapered portion.

12. The infusion device of claim 11, in which at least a portion of the septum is bounded by a portion of the body.

13. The infusion device of claim 12, in which the septum includes an outer wall extending from the septum bottom surface, the outer wall including an inwardly-tapered portion.

14. The infusion device of claim 13, in which the infusion device includes (a) a first distance between the septum top surface and the top of the body and (b) a second distance between the septum bottom surface and the adhesive bottom surface of the body, and the second distance is greater than the first distance.

15. The infusion device of claim 11, in which the septum includes an outer wall extending from the septum bottom surface, the outer wall including an inwardly-tapered portion.

16. The infusion device of claim 15, in which the infusion device includes (a) a first distance between the septum top surface and the top of the body and (b) a second distance between the septum bottom surface and the adhesive bottom surface of the body, and the second distance is greater than the first distance.

17. The infusion device of claim 11, in which the infusion device includes (a) a first distance between the septum top surface and the top of the body and (b) a second distance between the septum bottom surface and the adhesive bottom surface of the body, and the second distance is greater than the first distance.

18. The infusion device of claim 12, in which the infusion device includes (a) a first distance between the septum top surface and the top of the body and (b) a second distance between the septum bottom surface and the adhesive bottom surface of the body, and the second distance is greater than the first distance.

* * * * *